US005604119A

United States Patent [19]

Haraldsson et al.

[11] Patent Number: 5,604,119
[45] Date of Patent: Feb. 18, 1997

[54] PROCESS FOR PRODUCING TRIGLYCERIDES FROM GLYCEROL AND LONG-CHAIN POLYUNSATURATED FATTY ACIDS USING LIPASE FROM CANDIDA ANTARCTICA

[75] Inventors: Gudmundur G. Haraldsson, Reykjavik, Iceland; Hanne Svanholm, Soeborg, Denmark; Baldur Hjaltason, Reykjavik, Iceland

[73] Assignees: Novo Nordisk A/S, Bagsvaerd, Denmark; LYSI HF, Reykjavik, Iceland

[21] Appl. No.: 376,692

[22] Filed: Jan. 23, 1995

Related U.S. Application Data

[63] Continuation of Ser. No. 927,405, filed as PCT/DK91/00100, Apr. 16, 1991 published as WO91/16443, Oct. 31, 1991, abandoned.

[30] Foreign Application Priority Data

Apr. 18, 1990 [DK] Denmark ................................. 954/90

[51] Int. Cl.$^6$ ........................................................ C12P 7/64
[52] U.S. Cl. ............................................ 435/134; 435/922
[58] Field of Search ........................................ 435/134, 922

[56] References Cited

U.S. PATENT DOCUMENTS 5,273,898  12/1993  Ishii ........................................ 435/198

FOREIGN PATENT DOCUMENTS 0064855  11/1982  European Pat. Off. .
0322213  6/1989  European Pat. Off. .
62-91188  4/1987  Japan .
2205850  12/1988  United Kingdom .
WO89/01032  2/1989  WIPO .

OTHER PUBLICATIONS

Fujimoto et al., Chem. Abs., vol. 111, No. 25, p. 580, Abs. No. 230710w (1989).
Yamada et al., Chem. Abs., vol. 111, No. 17, p. 580, Abs. No. 152188r (1989).
Yamada et al., Chem. Abs., vol. 113, No. 11, p. 580, Abs. No. 96171g (1990).
Ergan et al, Biotech and Bioeng, 35(2):195–200 (Jan. 20, 1990).
Haraldsson et al, Tetrahedron Letters, 30(13):1671–1674(1989).
Cmbou et al.; J. Am. Chem. Soc., 106:2687–2692, (1984).
Tanaka et al, JAOCS, 69(20):1210–14, (Dec. 1992).
Ergan et al, Biotech Letters, 30(1):19–24, (1991).
Ergan et al., Biotech Letters, 13(1):19–24, (1991).
Osada et al., JAOCS, 67(12):921–922, (Dec. 1990).
Linfield et al, JAOCS, 61(2):191–195, (Feb. 1984).

*Primary Examiner*—Michael G. Wityshyn
*Assistant Examiner*—S. Saucier
*Attorney, Agent, or Firm*—Steve T. Zelson, Esq.; Elias J. Lambiris, Esq.

[57] ABSTRACT

The present invention relates to a process for preparing a triglyceride, comprising reacting glycerol with a polyunsaturated fatty acid having at least 20 carbon atoms and at least three double bonds or a $C_{1-4}$ alkyl ester thereof, for a reaction time in the range of 24–48 hours at a temperature between 40° and 80° C. in the presence of a mixture of lipase A and lipase B obtained from *Candida antarctica* which is immobilized, to form (i) the triglyceride and (ii) water or a $C_{1-4}$ alcohol, while removing the water or the $C_{1-4}$ alcohol during the reaction, and recovering the triglyceride.

14 Claims, No Drawings

PROCESS FOR PRODUCING TRIGLYCERIDES FROM GLYCEROL AND LONG-CHAIN POLYUNSATURATED FATTY ACIDS USING LIPASE FROM CANDIDA ANTARCTICA

CROSS-REFERENCE TO RELATED APPLICATIONS

This application is a continuation application of application Ser. No. 07/927,405, filed Sep. 25, 1992, now abandoned, which is a continuation of PCT/DK91/00,100 filed Apr. 16, 1991, which is incorporated herein by reference.

TECHNICAL FIELD

The invention relates to a process for the preparation of a triglyceride wherein all three fatty acids are $C_{20+}$ polyunsaturated fatty acids (with at least three double bonds), by esterification of glycerol with free polyunsaturated fatty acid or its $C_{1-4}$ lower alkyl ester in the presence of a lipase. The invention also relates to a triglyceride composition with a high content of polyunsaturated fatty acid.

BACKGROUND ART

It is known that triglycerides of poly-unsaturated fatty acid (PUFA), such as eicosapentaenoic acid (EPA) and docosahexaenoic acid (DHA), have beneficial medical effects, and within the last decade much attention has been directed to methods of producing triglyceride compositions with a high content of these acids, and particularly a high content of triglycerides with three such acids in the molecule.

PUFA in the form of free fatty acid or lower alkyl (e.g. methyl or ethyl) ester is available in high purity and have been used to prepare triglycerides with high PUFA content.

Thus, JP-A 61-43143 (Nisshin Flour Mill et al.) and EP 300,844 (R. F. Azar et al.) describe chemical interesterification of lower alkyl PUFA ester with triacetin or tributyrin. Sodium methylate was used as catalyst, and vacuum was used to remove lower alkyl acetate or butyrate formed in the reaction. The former describes production of triglyceride with 90% PUFA content.

JP-A 61-246146 (Nissui Seiyaku) describes halogenation of PUFA free acid, followed by reaction of PUFA acyl chloride with glycerine. The first step was carried out with oxalyl chloride at 65°–90° C. for 4 hours, and the second step under reflux for several hours in chloroform in the presence of quinoline or pyridine.

The above-mentioned processes use highly reactive chemicals that require special precautions in handling, these reactive chemicals react with part of the labile PUFA acyl groups, and the resulting reaction mixture in each case requires complex purification.

JP-A 62-91188 (Nisshin Oil) describes lipase-catalyzed production of PUFA glycerides from glycerol and PUFA free acid or ethyl ester, using positionally specific lipase in native form or immobilized on a weakly basic anion exchange resin. It is stated that addition of water is necessary. After reaction and removal of unreacted fatty acid, the glyceride mixture contained at most 86% triglyceride together with at least 14% diglyceride+monoglyceride. The product contained at most 85% polyunsaturated fatty acids together with at least 15% of other fatty acids.

It is an object of the invention to provide a simple process, avoiding the use of aggressive chemicals, to produce triglyceride with a low content of mono- and diglycerides, having a high content of PUFA, especially a high content of triglycerides with three PUFA in the molecule. It is also an object to provide triglyceride compositions with high PUFA content.

STATEMENT OF THE INVENTION

We have found that the yield of triglyceride can be increased and the amount of mono- and diglyceride decreased by removing water or lower alcohol formed during the reaction, by using positionally non-specific lipase, or by using a lipase immobilized by adsorption on a particulate, macroporous adsorbent resin of the acrylic type.

Accordingly, the invention provides a process for the preparation of a triglyceride wherein all three fatty acids are $C_{20+}$ polyunsaturated fatty acids (with at least three double bonds), by esterification of glycerol with free polyunsaturated fatty acid or its $C_{1-4}$ lower alkyl ester in the presence of a lipase. In the first aspect of the invention, the process is characterized by removing water or lower alcohol by evaporation during the reaction. In another aspect, the process is characterized in that the lipase is positionally non-specific. In a third aspect, the process is characterized in that the lipase is immobilized by adsorption on a particulate, macroporous adsorbent resin of the acrylic type.

The invention also provides a triglyceride composition, characterized by at least 95% by weight (preferably at least 98%) of the fatty acids in the triglyceride molecules being polyunsaturated $C_{18-22}$ acid.

DETAILED DESCRIPTION OF THE INVENTION

Polyunsaturated fatty acid

The process of the invention is applicable to $C_{20+}$ PUFA with 3 or more double bonds such as eicosapentaenoic acid (EPA, $C_{20:5}$) and docosahexaenoic acid (DHA, $C_{22:6}$).

Thus, the process of the invention can be used to prepare triglyceride compositions with high content of PUFA by using a reactant mixture wherein the free acid or lower alkyl ester contains at least 90%, preferably at least 95% and most preferably at least 98%, of PUFA. In this way it is possible to prepare triglyceride with PUFA in all three positions in good yield. In this connection, it has surprisingly been found that pure EPA or DHA is incorporated particularly fast.

Preferably, the PUFA reactant is free fatty acid, methyl or ethyl ester; These are easily available, and the resulting water, methanol or ethanol is very volatile and is easily removed.

The PUFA free fatty acid or ester may be prepared by known methods, and some are commercially available in high purity, e.g. EPA and DHA as free acid and ethyl ester in 99% purity from Idemitsu Petro Chemical Co., Ltd., Japan.

Lipase

The lipase should be sufficiently thermostable for the temperature and reaction time in question, e.g. 24 hours at 40°–80° C. It is preferred to use immobilized lipase.

One aspect of the invention uses a positionally non-specific lipase. Examples of non-specific lipases are those derived from strains of Candida, especially *C. antarctica* lipase (WO 88/02775, incorporated herein by reference), and lipase from *C. rugosa* (also known as *C. cylindracea*).

It is particularly preferred to use a lipase preparation containing both lipase A and lipase B of *C. antarctica* described in said reference.

Three strains of *C. antarctica* described in WO 88/02775 have been deposited at Deutsche Sammlung von Mikroroganismen (DSM) under the terms of the Budapest Treaty as follows:

| Deposit No. | Deposit date |
|---|---|
| DSM 3855 | September 29, 1986 |
| DSM 3908 | December 8, 1986 |
| DSM 3909 | December 8, 1986. |

Positionally specific (1,3-specific) lipase may be used in some embodiments of the invention. Examples are lipase derived from Humicola, especially *H. lanuginosa* (WO 89/06278) and recombinant *Humicola lipase* (EP 305,216) and Mucor lipase (EP 140,542).

One aspect of the invention uses iipase immobilized by adsorption on a particulate, macroporous adsorbent (i.e. non-ionic) resin of the acrylic type according to WO 89/02916.

An example of a lipase preparation that may be used is SP 382 from Novo Nordisk A/S (mixture of lipases A and B from *C. antarctica*, immobilized according to WO 89/02916).

Reaction conditions

A suitable amount of lipase is generally in the range 0.5–10 BIU/g (typically 1–5 BIU/g) of reactant mixture (BIU=Batch Interesterification Unit, see WO 89/06278) by use of immobilized lipase, or 50–500 LU/g of oil (LU= Upase Unit, see WO 88/02775) by use of native (non-immobilized) lipase.

It is preferable to use the two reactants at about the stoichiometric ratio or with a moderate excess (e.g. 0–50%, especially 0–20%) of the PUFA acid or ester. It is preferable to let the reaction continue until at least 90% (particularly more than 95, especially more than 98%) of the glycerol has been converted into triglyceride.

It is generally not necessary to use a pH buffer or an organic solvent in the process.

A temperature of 40°–80° C., especially 60°–80° C., is generally suitable for the reaction and the evaporation. The reaction time will generally be from 24–48 hours.

Removal of volatile alcohol or water

The removal by evaporation of volatile alcohol or water may be done continuously from a stirred tank. Reactants may be added batch wise, semi-batch wise or continuously. If the lipase is immobilized it can be separated off after the reaction and reused.

Alternatively, the reaction may occur in two or more steps, and evaporation can be done between the steps. Each process step can be made in a stirred tank, or immobilized iipase can be used continuously in a fixed bed.

The evaporation is most conveniently done under vacuum, e.g. below 200 Pa and especially below 20 Pa.

EXAMPLES

Example 1

Preparation of triglycerides containing approx. 85% EPA/DHA

Immobilized lipase derived from *Candida antarctica* (SP-382 from Novo Nordisk A/S; activity approx. 30 BIU/g; 1.53 g; moisture-free) was added to a mixture of glycerol (99% from Sigma; 1.37 g, 14.9 mmol) and 87% PUFA (free acid) concentrate (55% EPA and 32% DHA; M.wt. 311.0 g/mol; 14.1 g, 45.3 mmol). The mixture was gently stirred on a magnetic stirrer hot-plate at 65° C. under continuous vacuum of 0.1 mm Hg. The volatile water or lower alcohol, when using lower alkyl ester concentrates, produced during the progress of the reaction was continuously condensed into a liquid nitrogen cooled trap, which could be separated and weighed regularly during the process by disconnecting the reaction by replacing the vacuum with dry nitrogen or argon atmosphere. After 30 hours the reaction was discontinued, hexane added and the enzyme separated off by filtration. The hexane was removed in vacuo on a rotary evaporator. Titration was applied to determine the free fatty acid content of the crude reaction product (3% FFA content, corresponding to 97% incorporation, which is equivalent to 91% triglyceride content). The titration results were confirmed by Iatroscan studies, which indicated 91% triglyceride content, after the product had been freed from free fatty acids by washing the organic phase a few times with 0.25M sodium hydroxide in 1:1 water/ethanol solution. 100% pure triglycerides were afforded by preparatory High Performance Liquid Chromatography (HPLC) eluting with 10% ether in hexane solvent, which was confirmed by Iatroscan studies. Capillary Gas Liquid Chromatography (GLC) analysis showed fatty acid composition identical to the original PUFA concentrate.

The following equation was used to calculate the % incorporation of fatty acids into glycerol from the weight measurements:

$$\%incorporation = 1.71 \cdot [Wt_{water}/Wt_{glycerol}] \cdot 100\%$$

This was deduced from the following equation:

% incorp. =
1/3 · [# of eq. of entrapped water/# of eq. of glycerol used] ·
100% = 1/3 · [$Wt_{water}/M \cdot wt_{water}$]/[$Wt_{glycerol}/M \cdot wt_{glycerol}$] ·
100% = 1/3 · [$Wt_{water}/Wt_{glycerol}$] · [$M \cdot wt_{glycerol}/M \cdot wt_{water}$] ·
100% = 1/3 · [$Wt_{water}/Wt_{glycerol}$] · [92.1/18.0] · 100% =

$$1.71 \cdot [Wt_{water}/Wt_{glycerol}] \cdot 100\%$$

The following results were obtained:

| Time | % incorporation* | |
|---|---|---|
| hours | min.* | max.* |
| 1 | 50 | 56 |
| 2 | 67 | 72 |
| 6 | 90 | 96 |
| 24 | 103** | 108 |
| 30 | 103** | 108 |

*The incorporation was determined by mass measurements of the entrapped product. The minimum incorporation was based on the assumption that all the moisture had escaped from the immobilized lipase.
**Due to inaccuracy in the mass measurements the minimum incorporation passes the 100% incorporation level.

Example 2

Preparation of triglycerides containing approx. 60–70% EPA/DHA

The procedure of Example 1 was followed in details by using immobilized lipase SP-382 (1.10 g; 10% moisture content), which was added to a mixture of glycerol (1.00 g, 10.9 mmol) and 66% PUFA concentrate (38% EPA and 28% DHA; M.wt. 309.5 g/mol; 10.2 g, 33.0 mmol) or 59% PUFA concentrate (29% EPA and 30% DHA; M.wt. 306.4 g/mol; 10.1 g; 33.0 mmol).

The following results were found:

| Time, hours | % incorporation* | | | |
|---|---|---|---|---|
| | 59% PUFA | | 66% PUFA | |
| | min. | max. | min. | max. |
| 1 | 53 | 72 | 34 | 53 |
| 2 | 67 | 85 | 61 | 80 |
| 3 | 77 | 96 | 73 | 92 |
| 6 | 89 | 108 | 79 | 97 |
| 24 | 106** | 125 | 90 | 109 |
| 28 | 106** | 125 | 90 | 109 |

*The incorporation was determined by mass measurements of the entrapped product. The minimum incorporation was based on the assumption that all the moisture had escaped from the immobilized lipase.
**Due to inaccuracy in the mass measurements the minimum incorporation passes the 100% incorporation level.

Example 3

Preparation of triglycerides containing 99% EPA

Immobilized lipase SP 382 (0.50 g; moisture-free) was added to a mixture of glycerol (99% from Sigma; 0.44 g, 4.78 mmol) and 99% EPA as free fatty acids (M.wt. 302.5 g/mol; 4.40 g, 14.54 mmol). The mixture was gently stirred on a magnetic stirrer hot-plate at 65° C. under continuous vacuum of 0.5–0.1 mmHg. The volatile water produced during the progress of the reaction was continuously condensed into a liquid nitrogen cooled trap, which could be separated and weighed regularly during the process by disconnecting the reaction by replacing the vacuum with dry nitrogen or argon atmosphere. After 30 hours the reaction was discontinued, hexane added and the enzyme separated off by filtration. The organic solvent was removed in vacuo on a rotary evaporator to afford the crude product as a slightly yellowish oil (4.18 g, 93%). Weight measurements indicated 105–108% incorporation, but NMR spectroscopy indicated 98% incorporation, which had increased to 99% after 48 hours. Titration was applied to determine the free acid content of the crude reaction product (less than 1% FFA content, corresponding to at least 99% incorporation, which is equivalent to 97% triglyceride content). The crude product was directly introduced into HPLC eluting with 10% ether in hexane solvent to afford 100% pure triglycerides (3.51 g, 84% recovery from HPLC, but overall yield 78%) which was confirmed by iatroscan studies.

[250 MHz-$^1$H NMR (CDCl$_3$): $\delta$5.41–5.26 (m, 31 H, =C—H and —CH$_2$—CH—CH$_2$—), 4.30 (dd,J=11.90 Hz, J=4.34 Hz, 2 H, —CH$_2$—CH—CH$_2$—), 4.14 (dd,J=11.90 Hz, J=5.93 Hz, 2 H, —CH$_2$—CH—CH$_2$—), 2.90–2.78 (m, 24 H,=C—CH$_2$—C=), 2.33(t,J=7.34 Hz, 2H, OOC—CH$_2$—), 2.32 (t,J=7.36 Hz, 4 H, OOC—CH$_2$—), 2.15–2.01 (m, 12 H, —CH$_2$—CH$_2$—C=), 1.75–1.61 (m, 6H, =CH—CH$_2$—CH$_3$), and 0.97 ppm (t,J=7.52 Hz, 9 H, —CH$_3$). $^{13}$C NMR (CDCl$_3$): $\delta$172.9(s), 172.6(s), 132.0(d), 128,9(d), 128.7(d), 128.5(d), 128.2(d), 128.1(d), 128.1(d), 128.0(d), 127.8(d), 127.0(d), 68.9(d), 62.1(t), 33.5(t), 33.3(t), 26.4(t), 25.6(t), 25.6(t), 25.5(t), 24.7(t), 24.6(t), 20.5(t) and 14.2 ppm(q), IR (neat liquid): $v_{max}$ 3020 (vs,C=C—H), 2970 (s, CH$_3$), 2935 (s, CH$_2$), 2875 (s, CH$_3$), 2850 (w, CH$_2$), 1745 (vs, C=O) and 1645 cm$^{-1}$ (ms, C=C). m/e (EI): 945 (M$^+$, 100%); found 944.68784 C$_{63}$H$_{92}$O$_6$ requires 944.68939 amu].

The following results were obtained:

| Time | % incorporation | | |
|---|---|---|---|
| hours | min.* | max.* | NMR |
| 1 | 56 | 62 | 60 |
| 2 | 72 | 78 | 74 |
| 4 | 91 | 97 | 89 |
| 6 | 92 | 98 | 91 |
| 12 | 95 | 101 | 96 |
| 24 | 99 | 105 | 97 |
| 30 | 99 | 105 | 98 |
| 48 | 99 | 105 | 99 |

*The incorporation was determined by mass measurements of the entrapped product. The minimum incorporation was based on the assumption that all the moisture had escaped from the immobilized lipase.

Example 4

Preparation of triglycerides containing 99% DHA

Immobilized lipase SP 382 (0.50 g; moisture-free) was added to a mixture of glycerol (99% from Sigma; 0.41 g, 4.45 mmol) and 99% DHA as free fatty acids (M.wt. 328.5 g/mol; 4.43 g, 13.48 mmol). The mixture was gently stirred on a magnetic stirrer hot-plate at 65° C. under continuous vacuum of 0.5–0.1 mmHg. The volatile water produced during the progress of the reaction was continuously condensed into a liquid nitrogen cooled trap, which could be separated and weighed regularly during the process by disconnecting the reaction by replacing the vacuum with dry nitrogen or argon atmosphere. After 30 hours the reaction was discontinued, hexane added and the enzyme separated off by filtration. The organic solvent was removed in vacuo on a rotary evaporator to afford the crude product as a slightly yellowish oil (4.36 g, 95%). Weight measurements indicated 100–106% incorporation which remained constant from 24 to 72 hours, whereas NMR spectroscopy indicated 97% incorporation after 24 hours which had increased to 100% after 72 hours. The crude product was directly introduced into HPLC eluting with 10% ether in hexane solvent to afford pure triglycerides (3.46 g, 80% recovery from HPLC, but overall yield 76%) which was confirmed by iatroscan studies.

[250 MHz $^1$H NMR (CDCl$_3$): $\delta$5.44–5.25 (m, 37 H, =C—H and —CH$_2$—CH—CH$_2$—), 4.30 (dd,J=11.90 Hz, J=4.36 Hz, 2 H, —CH$_2$—CH—CH$_2$—), 4.15 (dd,J=11.90 Hz, J=5.89 Hz, 2 H, —CH$_2$—CH—CH$_2$—), 2.90–2.79 (m, 30 H, =C—CH$_2$—C=), 2.39–2.38 (m, A$_2$B$_2$, 12 H, =CH—CH$_2$—CH$_2$—COOH), 2.13–2.02 (m, 6 H, =CH—CH$_2$—CH$_3$), and 0.97 ppm (t,J=7.53 Hz, 9 H, —CH$_3$). $^{13}$C NMR (CDCl$_3$): $\delta$172.5(s), 172.1(s), 132.0(d), 129.5(d), 128.5(d), 128.3(d), 128.3(d), 128.2(d), 128.2(d), 128.0(d), 127.9(d), 127.8(d), 127.6(d), 127.0(d), 69.0(d), 62.2(t), 34.0(t), 33.8(t), 25.6(t), 25.6(t), 25.6(t), 25.6(t), 25.5(t), 22.6(t), 20.5(t) and 14.2 ppm(q), IR (neat liquid): $v_{max}$ 3020 (vs,C=C—H), 2970 (S, CH$_3$), 2930 (s, CH$_2$), 2870 (s, CH$_3$), 2850 (w, CH$_2$), 1750 (vs, C=O) and 1650 cm$^{-1}$ (ms, C=C). m/e (EI): 1023 (M$^+$, 100%); found 1022.7340 C$_{69}$H$_{98}$O$_6$ requires 1022.7363 amu].

The following results were obtained:

| Time | % incorporation | | |
|---|---|---|---|
| hours | min.* | max.* | NMR |
| 1 | 18 | 24 | 24 |
| 2 | 43 | 49 | 45 |
| 4 | 59 | 65 | 67 |
| 6 | 71 | 77 | 77 |
| 12 | 91 | 97 | 91 |
| 24 | 100 | 106 | 97 |
| 30 | 100 | 106 | 98 |
| 48 | 100 | 106 | 99 |
| 72 | 100 | 106 | 100 |

*The incorporation was determined by mass measurements of the entrapped product. The minimum incorporation was based on the assumption that all the moisture had escaped from the immobilized lipase.

Example 5

Preparation of triglycerides with reuse of lipase

Immobilized lipase SP-382 (9.31 g; moisture-free) was added to a mixture of glycerol (9.00 g; 97.7 mmol) and free fatty acids from cod liver oil (9% EPA and 9% DHA; M.wt. 285.0 g/mol; 84.1 g; 295 mmol). The mixture was gently stirred at 65° C. under a continuous vacuum of 0.1 mm Hg. The volatile water produced during the progress of the reaction was condensed into a liquid nitrogen cooled trap, which was weighed regularly during the progress of the reaction. After 48 hours the reaction was discontinued and the lipase directly separated off without an organic solvent by filtration under dry nitrogen by the aid of a pressure equalized funnel equipped with a sintered glass filter plate and inlets/outlets to the nitrogen and the vacuum lines to aid the filtration, which was controlled by teflon key stopcocks. The oil was collected for further analysis.

The immobilized lipase was reintroduced into the reaction vessel. This was repeated 5 times, reusing the same immobilized lipase.

The following results were obtained:

| Run | % incorporation* | |
|---|---|---|
| No. | min. | max. |
| 1 | 93 | 96 |
| 2 | 93 | 97 |
| 3 | 93 | 97 |
| 4 | 93 | 97 |
| 5 | 94 | 98 |

*As determined by mass measurements of the entrapped product after 48 hours.

We claim:

1. A process for preparing a triglyceride, comprising:
   (a) reacting glycerol with a polyunsaturated fatty acid having at least 20 carbon atoms and at least three double bonds or a $C_{1-4}$ alkyl ester thereof, for a reaction time in the range of 24–48 hours at a temperature between 40° and 80° C. in the presence of a mixture of lipase A and lipase B obtained from *Candida antarctica* which is immobilized, to form (i) the triglyceride and (ii) water or a $C_{1-4}$ alcohol, while removing the water or the $C_{1-4}$ alcohol during the reaction, wherein the reaction converts at least 90% of the glycerol into the triglyceride, and
   (b) recovering the triglyceride.

2. The process according to claim 1, wherein the temperature of the reaction is between 60° and 80° C.

3. The process according to claim 1, wherein the water or the $C_{1-4}$ alcohol is removed by evaporation.

4. The process according to claim 3, wherein the water or the $C_{1-4}$ alcohol is removed under vacuum below 20 Pa.

5. The process according to claim 1, wherein the mixture of lipase A and lipase B is immobilized by adsorption on a particulate, macroporous adsorbent resin.

6. The process according to claim 5, wherein the mixture of lipase A and lipase B is immobilized by adsorption on a particulate, macroporous adsorbent resin of the acrylic type.

7. The process according to claim 1, wherein the fatty acid or $C_{1-4}$ alkyl ester thereof is at least 90% pure.

8. The process according to claim 1, wherein no buffer or organic solvent is used.

9. The process according to claim 1, wherein the reaction time is from 24 to 30 hours.

10. The process according to claim 1, wherein the reaction time is at least 30 hours.

11. The process according to claim 1, wherein the polyunsaturated fatty acid is eicosapentenoic acid or docosahexenoic acid.

12. The process according to claim 1, wherein the polyunsaturated fatty acid or $C_{1-4}$ alkyl ester thereof is a methyl or ethyl ester thereof.

13. The process according to claim 1, wherein a stoichiometric excess of 0–50% of the polyunsaturated fatty acid or $C_{1-4}$ alkyl ester thereof relative to glycerol is used.

14. The process according to claim 13, wherein a stoichiometric excess of 0–20% of the polyunsaturated fatty acid or $C_{1-4}$ alkyl ester thereof relative to glycerol is used.

* * * * *